US012098981B2

(12) United States Patent
    Peterson

(10) Patent No.: US 12,098,981 B2
(45) Date of Patent: Sep. 24, 2024

(54) ROBOTIC SOIL SAMPLING ASSEMBLY

(71) Applicant: Jeffrey M. Peterson, Watertown, SD (US)

(72) Inventor: Jeffrey M. Peterson, Watertown, SD (US)

( * ) Notice: Subject to any disclaimer, the term of this patent is extended or adjusted under 35 U.S.C. 154(b) by 294 days.

(21) Appl. No.: 17/840,004

(22) Filed: Jun. 14, 2022

(65) Prior Publication Data

US 2023/0400389 A1    Dec. 14, 2023

(51) Int. Cl.
    *G01N 1/08*        (2006.01)
    *G01N 1/02*        (2006.01)
    *G01N 33/24*       (2006.01)

(52) U.S. Cl.
    CPC .............. *G01N 1/08* (2013.01); *G01N 33/24* (2013.01); *G01N 2001/021* (2013.01)

(58) Field of Classification Search
    None
    See application file for complete search history.

(56) References Cited

U.S. PATENT DOCUMENTS

| | | | |
|---|---|---|---|
| 5,887,491 A | 3/1999 | Monson |
| 6,363,803 B1 | 4/2002 | Hubers |
| 9,500,567 B2 | 11/2016 | Scheiderer |
| 9,759,637 B1 | 9/2017 | Hellbusch |

FOREIGN PATENT DOCUMENTS

| | | | | |
|---|---|---|---|---|
| CA | 3142363 A1 | * | 5/2018 | .......... A01B 79/005 |
| CN | 20099297 | | 12/2007 | |
| CN | 105372092 | | 12/2017 | |
| CN | 110411784 | | 11/2019 | |
| CN | 211692302 | | 10/2020 | |
| CN | 114235472 A | * | 3/2022 | |

* cited by examiner

*Primary Examiner* — Peter J Macchiarolo
*Assistant Examiner* — Jermaine L Jenkins

(57) ABSTRACT

A robotic soil sampling assembly for rapidly obtaining a soil sample from each of multiple sites includes a rolling chassis, to which a sampling apparatus and a computer are attached. The sampling apparatus comprises an auger, a plurality of containers, a robotic manager, and a robotic handler. The robotic manager selectively positions a respective container in axial alignment with the auger, whereupon it is selectively gripped by the robotic handler and selectively positioned along an axis that is defined by the auger. A drill motor and a drill actuator selectively rotate and drill the auger, respectively, into ground upon which the rolling chassis is positioned. The computer is programmed to selectively actuate a pair of chassis motors to sequentially position the rolling chassis at sampling sites and to selectively actuate the sampling apparatus for obtaining a soil sample, which is deposited into an associated container.

15 Claims, 13 Drawing Sheets

ROBOTIC SOIL SAMPLING ASSEMBLY

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

CORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to soil sampling assemblies and more particularly pertains to a new soil sampling assembly for rapidly obtaining a soil sample from each of multiple sites. The present invention discloses a soil sampling assembly comprising a rolling chassis, to which a computer and sampling apparatus comprising an auger are attached, which greatly reduces the labor involved in obtaining soil samples, particularly from hard soils.

(2) Description of Related Art Including Information Disclosed Under 37 CFR 1.97 and 1.98

The prior art relates to soil sampling assemblies, which may comprise computer controlled rolling chassis to which sampling apparatuses for hydraulic sampling are attached. The sampling apparatuses comprise rotatable plates, which are slidable relative to the rolling chassis and to which containers are attached. The containers are selectively positionable under the sampling apparatuses. What is lacking in the prior art is a soil sampling assembly comprising a rolling chassis, to which a computer and sampling apparatus comprising an auger are attached. Also lacking in the prior art is a sampling apparatus comprising a robotic manager and a robotic handler for positioning the containers, first in axial alignment with the auger, and secondly along an axis that is defined by the auger.

BRIEF SUMMARY OF THE INVENTION

An embodiment of the disclosure meets the needs presented above by generally comprising a rolling chassis, to which a sampling apparatus and a computer are attached. The sampling apparatus comprises a drill assembly, a plurality of containers, to which a robotic manager is operationally engaged, and a robotic handler. The drill assembly comprises an auger, to which a drill motor and a drill actuator are operationally engaged.

The robotic manager selectively positions a respective container in axial alignment with the auger. With the respective container thus positioned, the robotic handler is positioned to selectively grip the respective container and to selectively position the respective container along an axis that is defined by the auger. With the respective container abutting a surface of the ground upon which the rolling chassis is positioned, the drill motor and a drill actuator selectively rotate and drill the auger, respectively, into the ground.

The computer is operationally engaged to the rolling chassis and to the sampling apparatus. The computer is programmable to sequentially position the rolling chassis at sampling sites and to selectively actuate the sampling apparatus for obtaining a soil sample at each sampling site and for depositing the soil sample in an associated container.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

Figure 3:
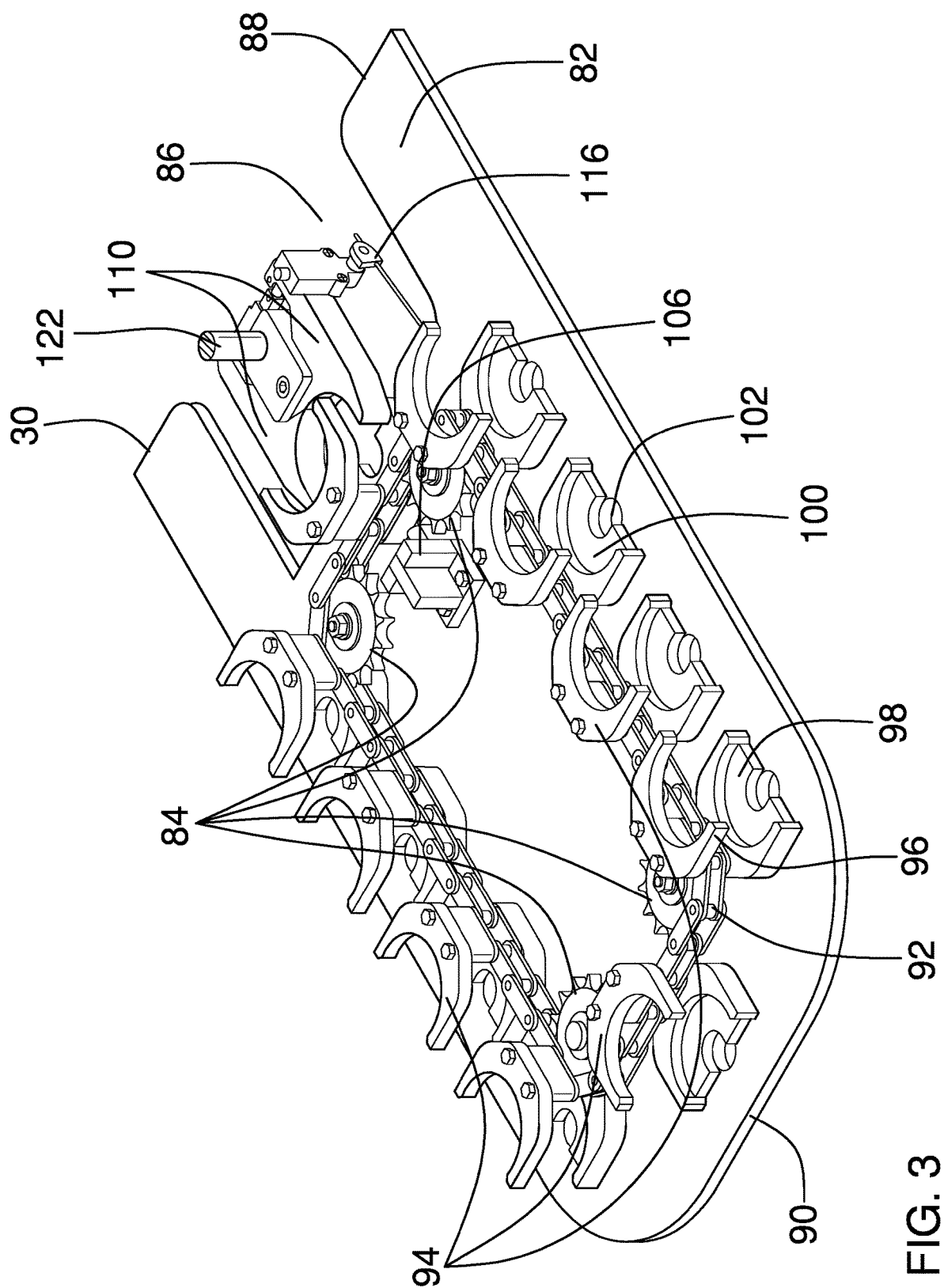
Figure 4:
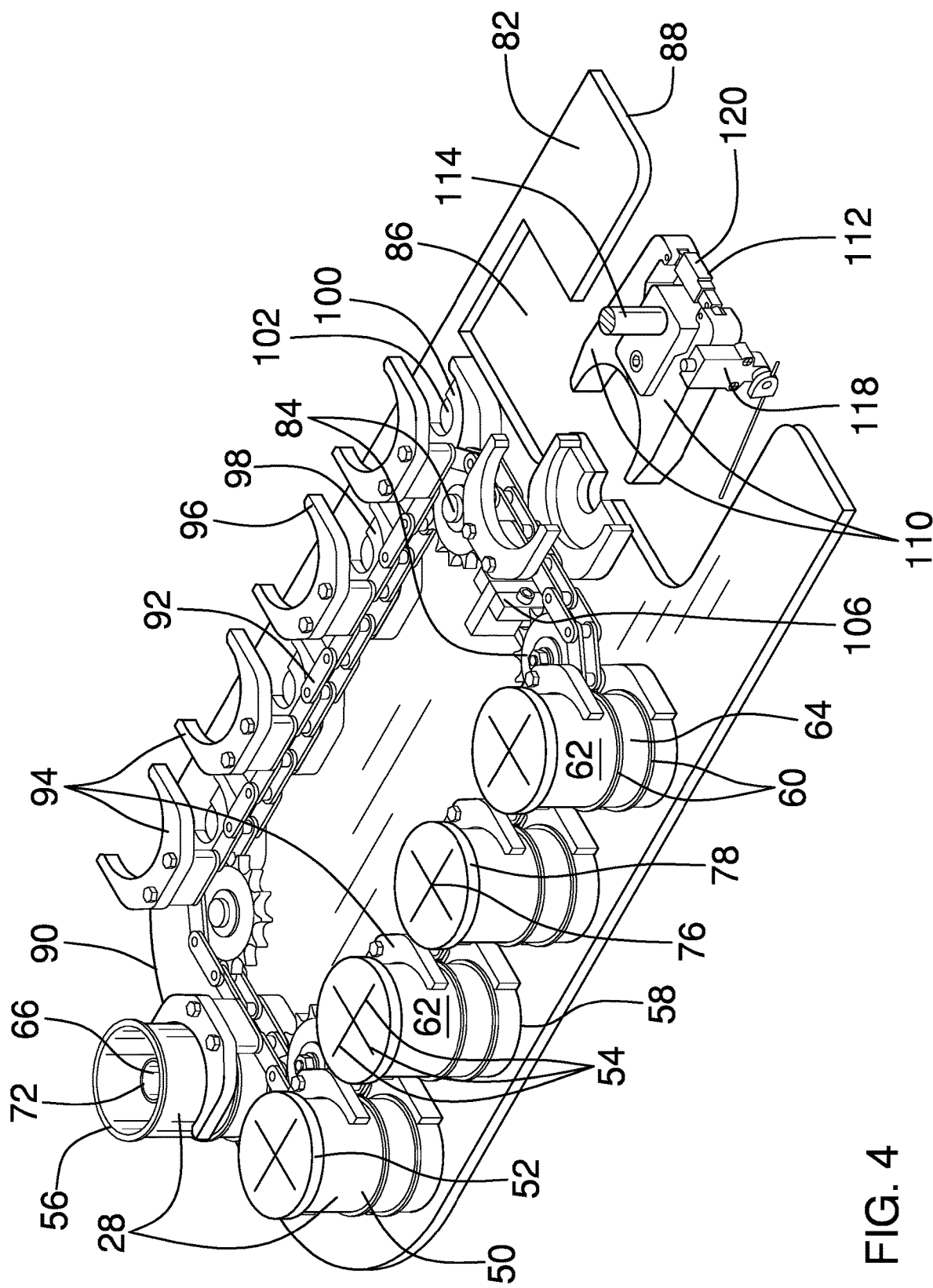
Figure 5:
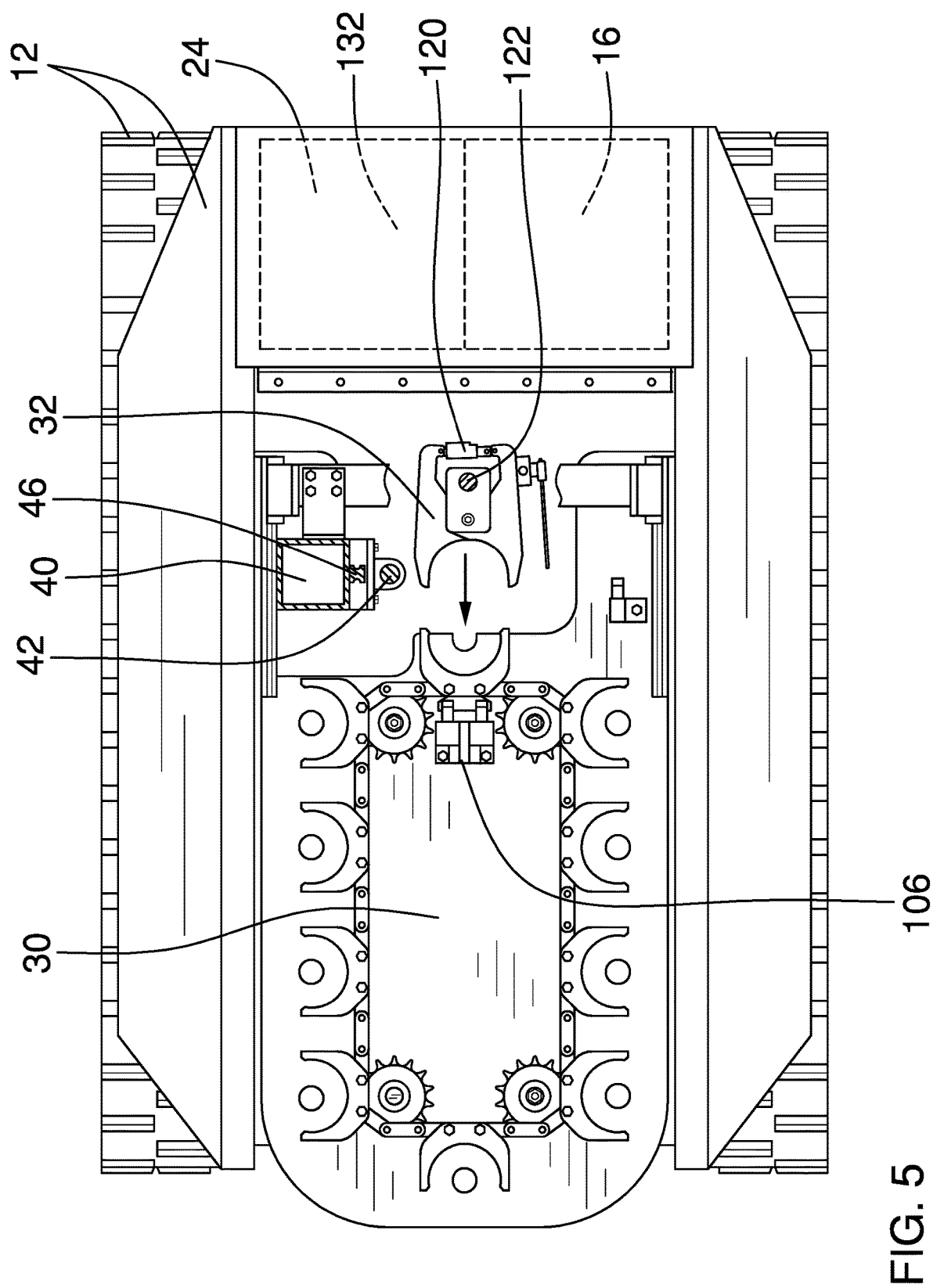
Figure 6:
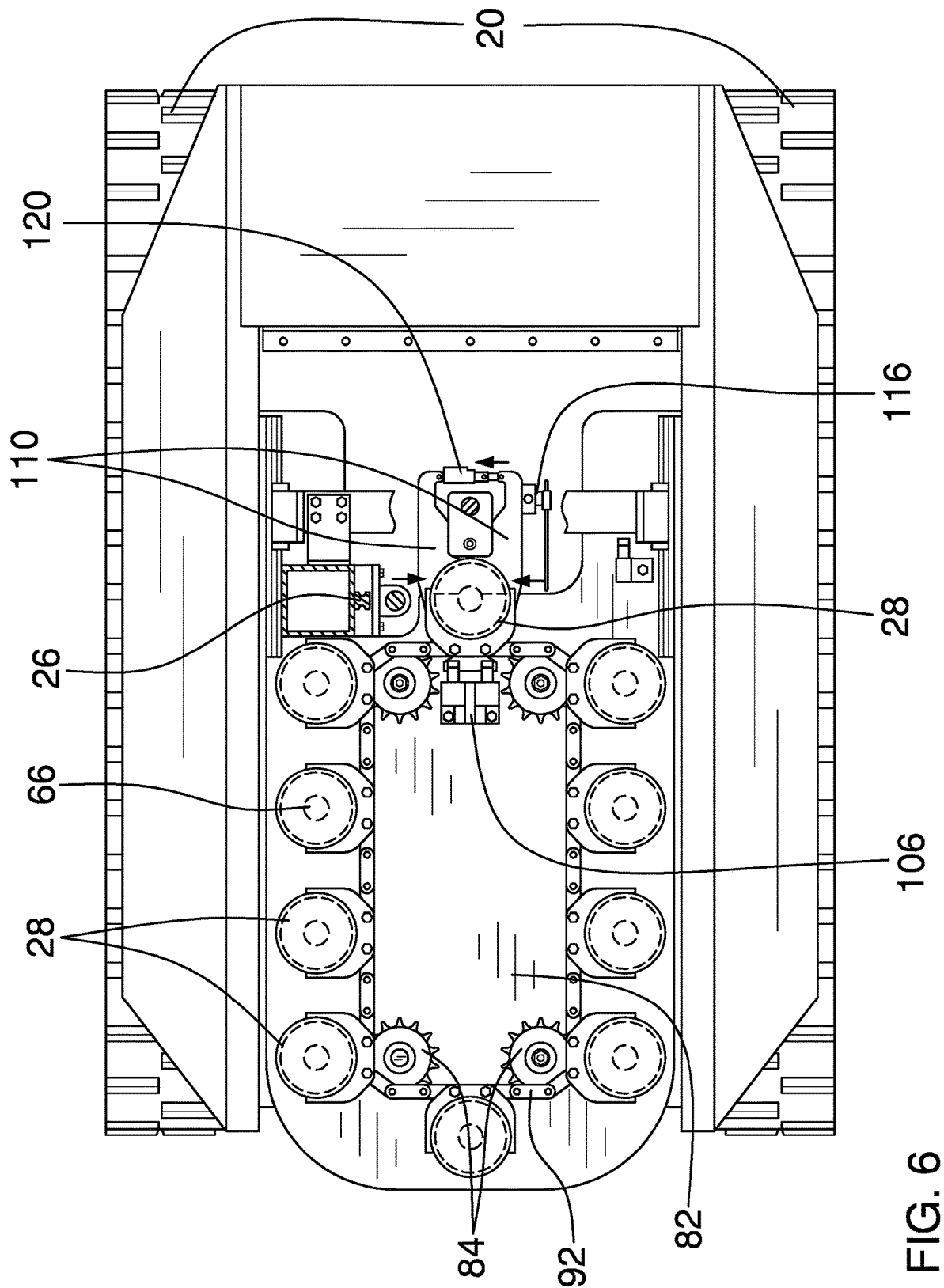
Figure 7:
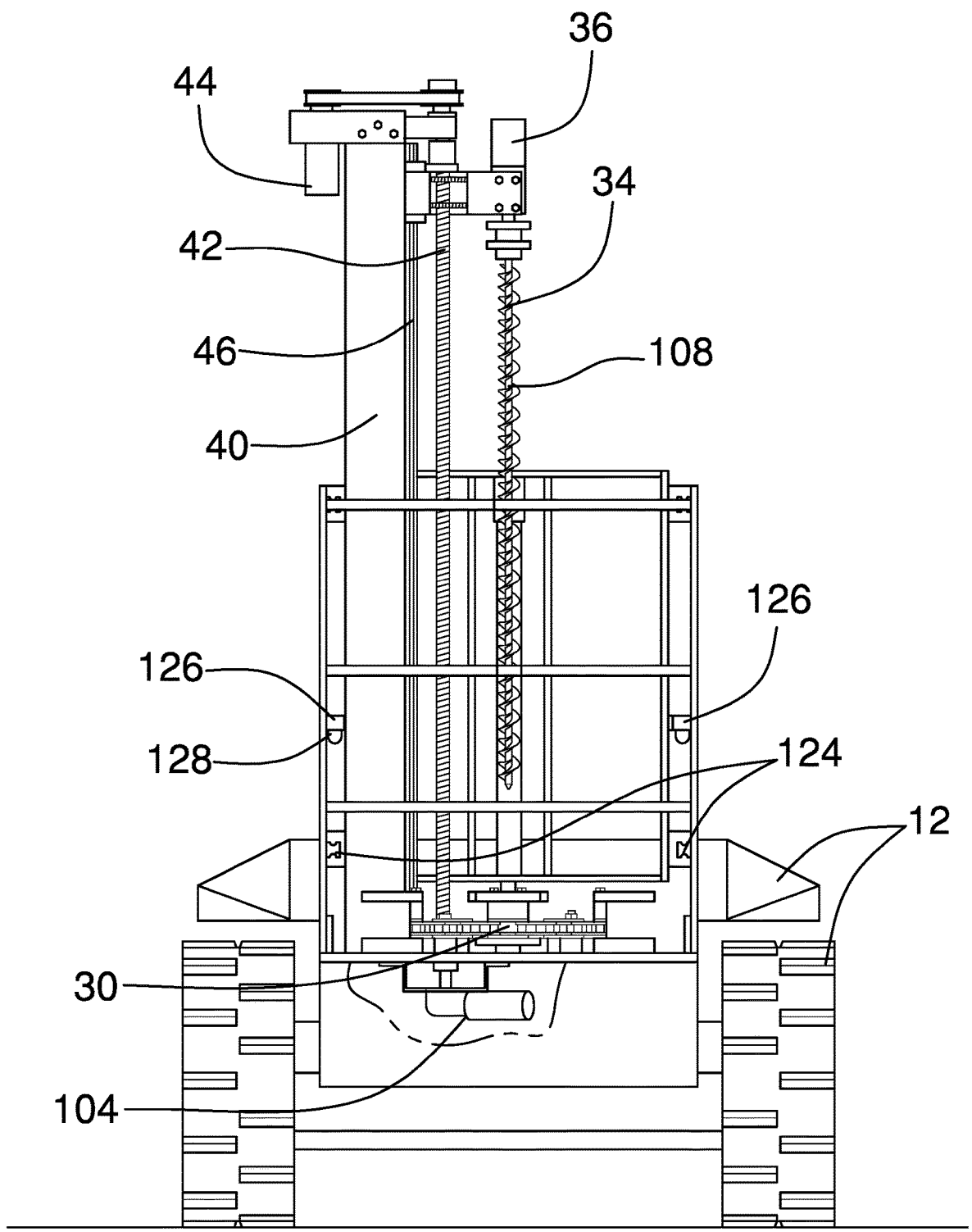
Figure 8:
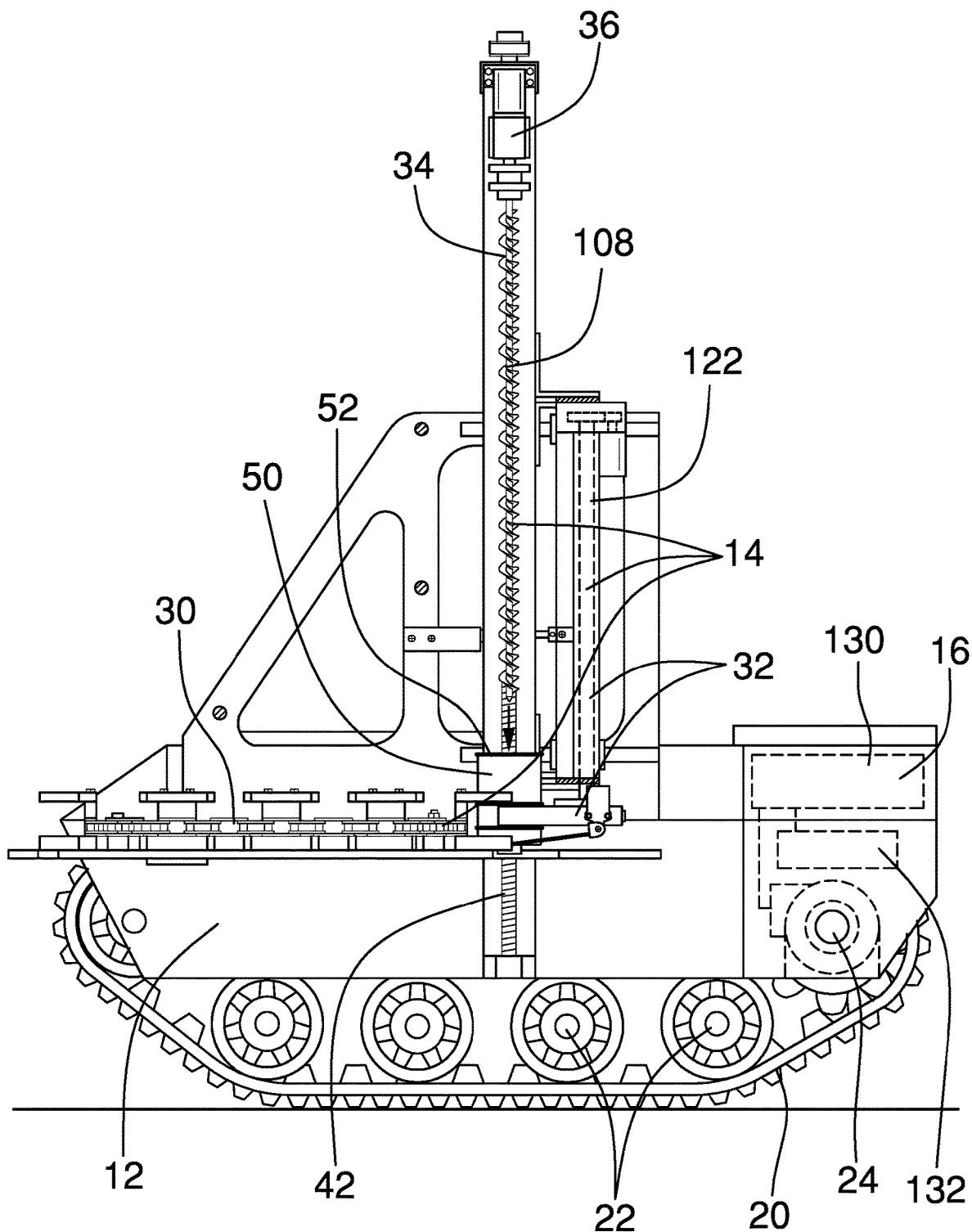
Figure 9:
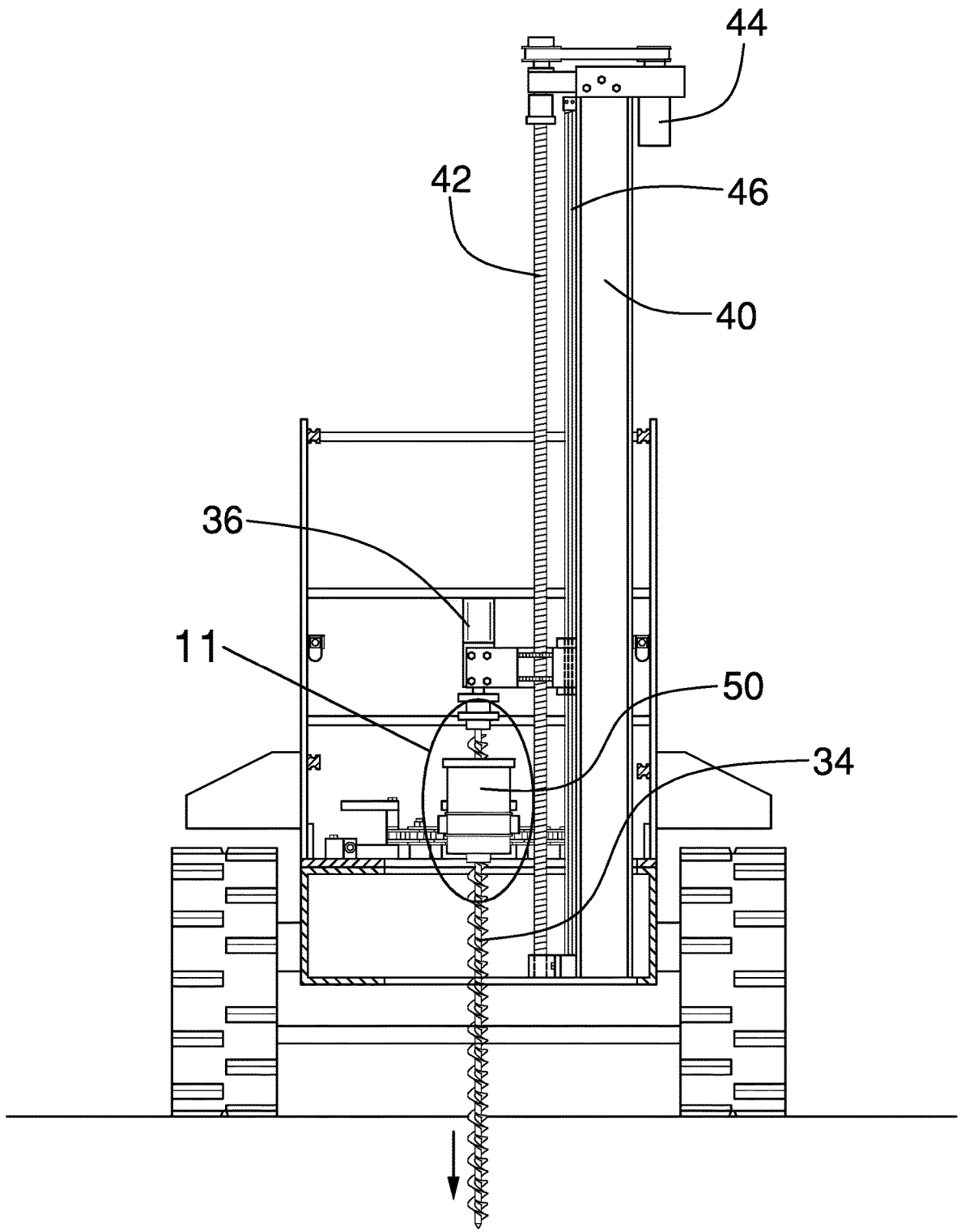
Figure 10:
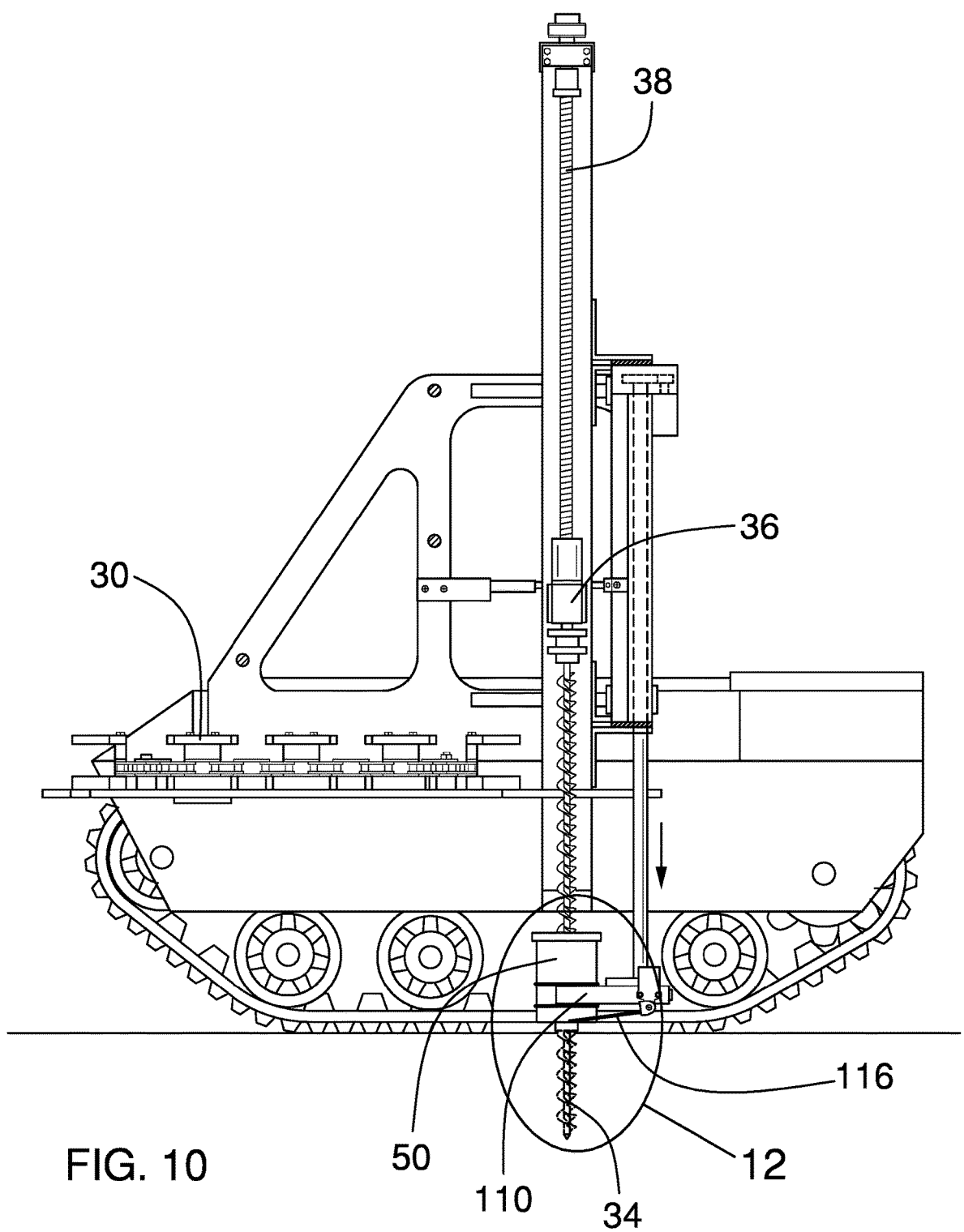
Figure 11:
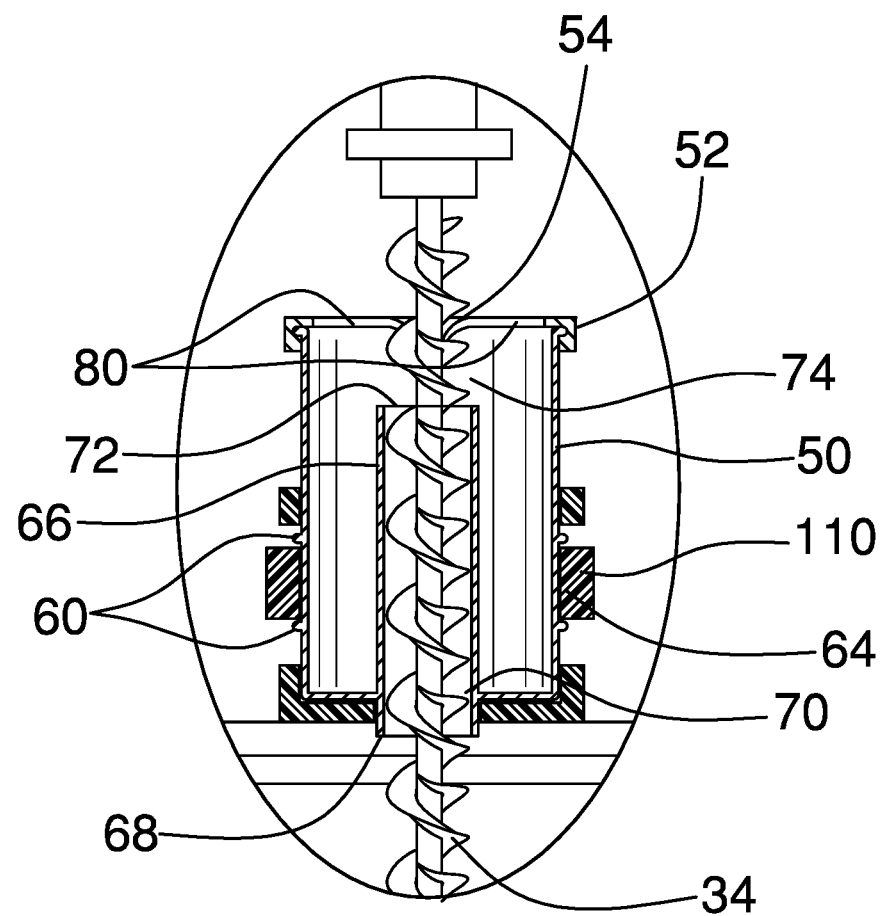
Figure 12:
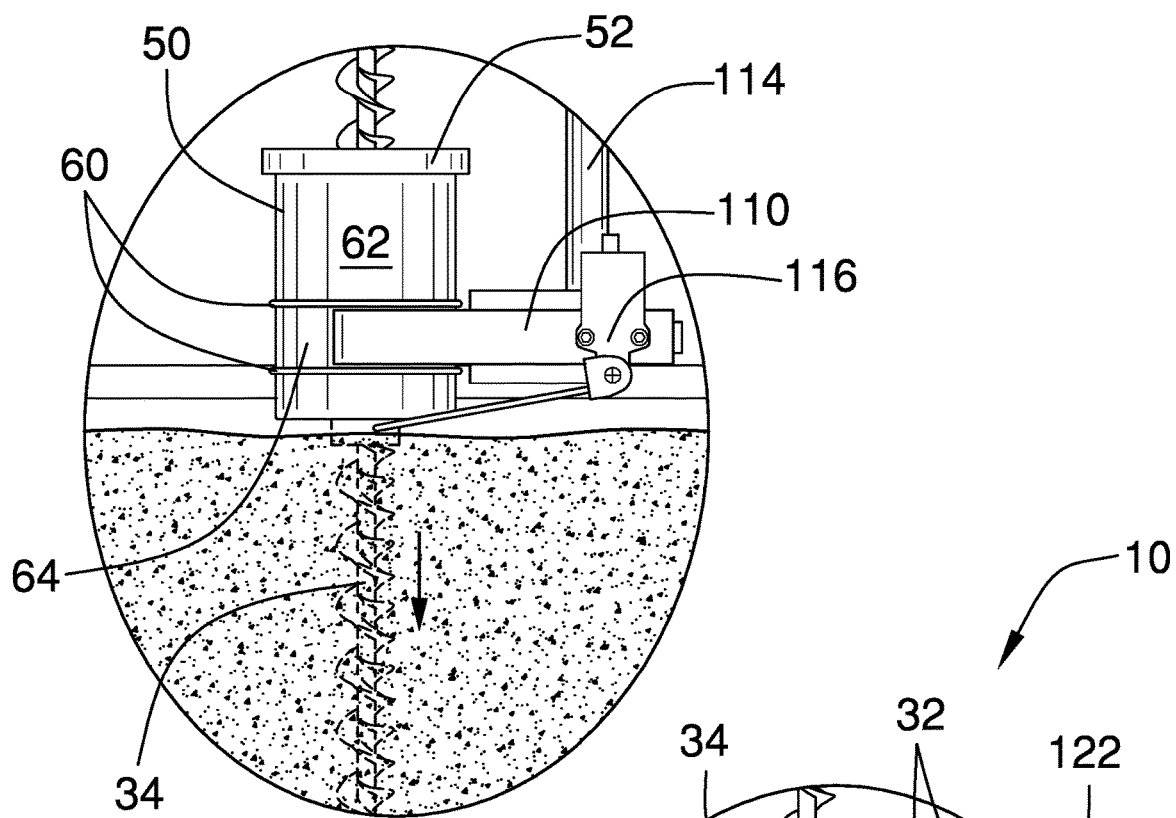
Figure 13:
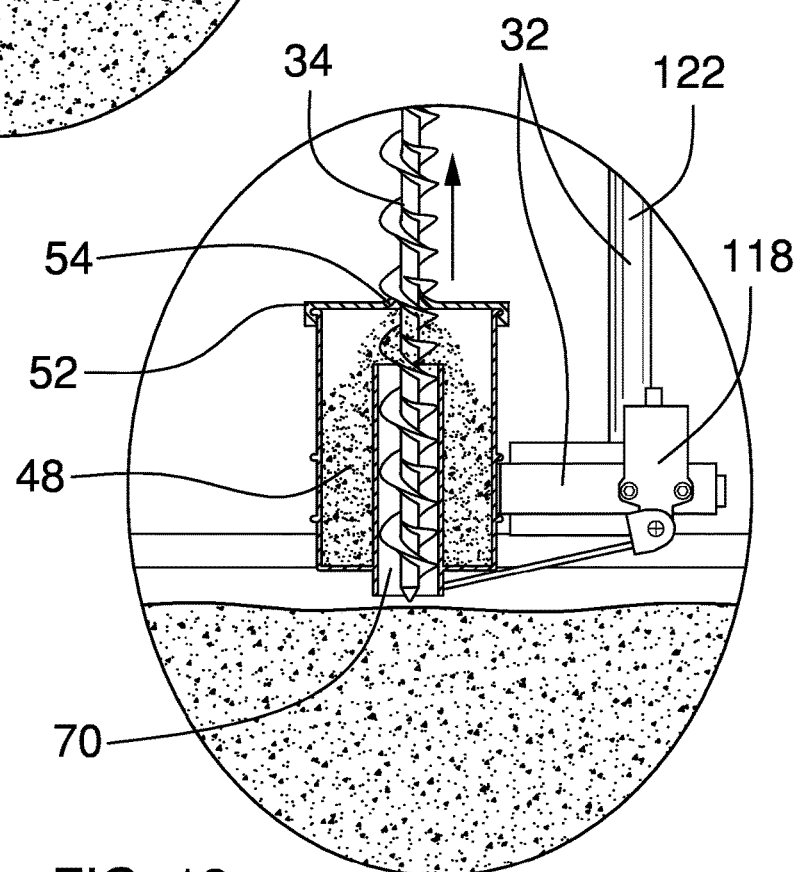
Figure 14:
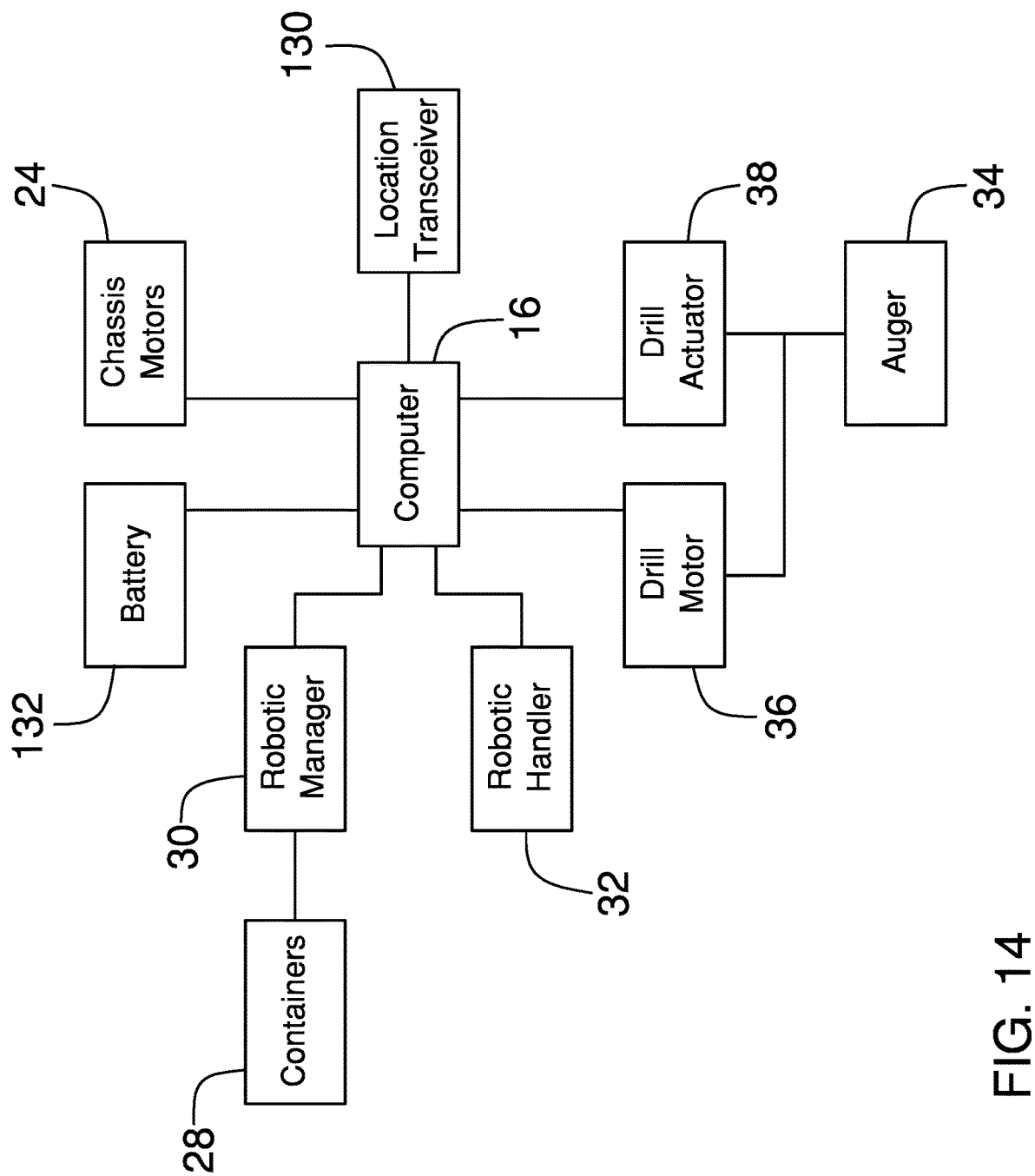

FIG. 3 is a detail view of an embodiment of the disclosure.
FIG. 4 is a detail view of an embodiment of the disclosure.
FIG. 5 is a top view of an embodiment of the disclosure.
FIG. 6 is a top view of an embodiment of the disclosure.
FIG. 7 is a front view of an embodiment of the disclosure.
FIG. 8 is a side view of an embodiment of the disclosure.
FIG. 9 is a rear view of an embodiment of the disclosure.
FIG. 10 is an in-use view of an embodiment of the disclosure.
FIG. 11 is a detail view of an embodiment of the disclosure.
FIG. 12 is a detail in-use view of an embodiment of the disclosure.
FIG. 13 is a detail in-use view of an embodiment of the disclosure.
FIG. 14 is block diagram of an embodiment of the disclosure.

DETAILED DESCRIPTION OF THE INVENTION

With reference now to the drawings, and in particular to FIGS. 1 through 14 thereof, a new soil sampling assembly embodying the principles and concepts of an embodiment of the disclosure and generally designated by the reference numeral 10 will be described.

Figure 1:
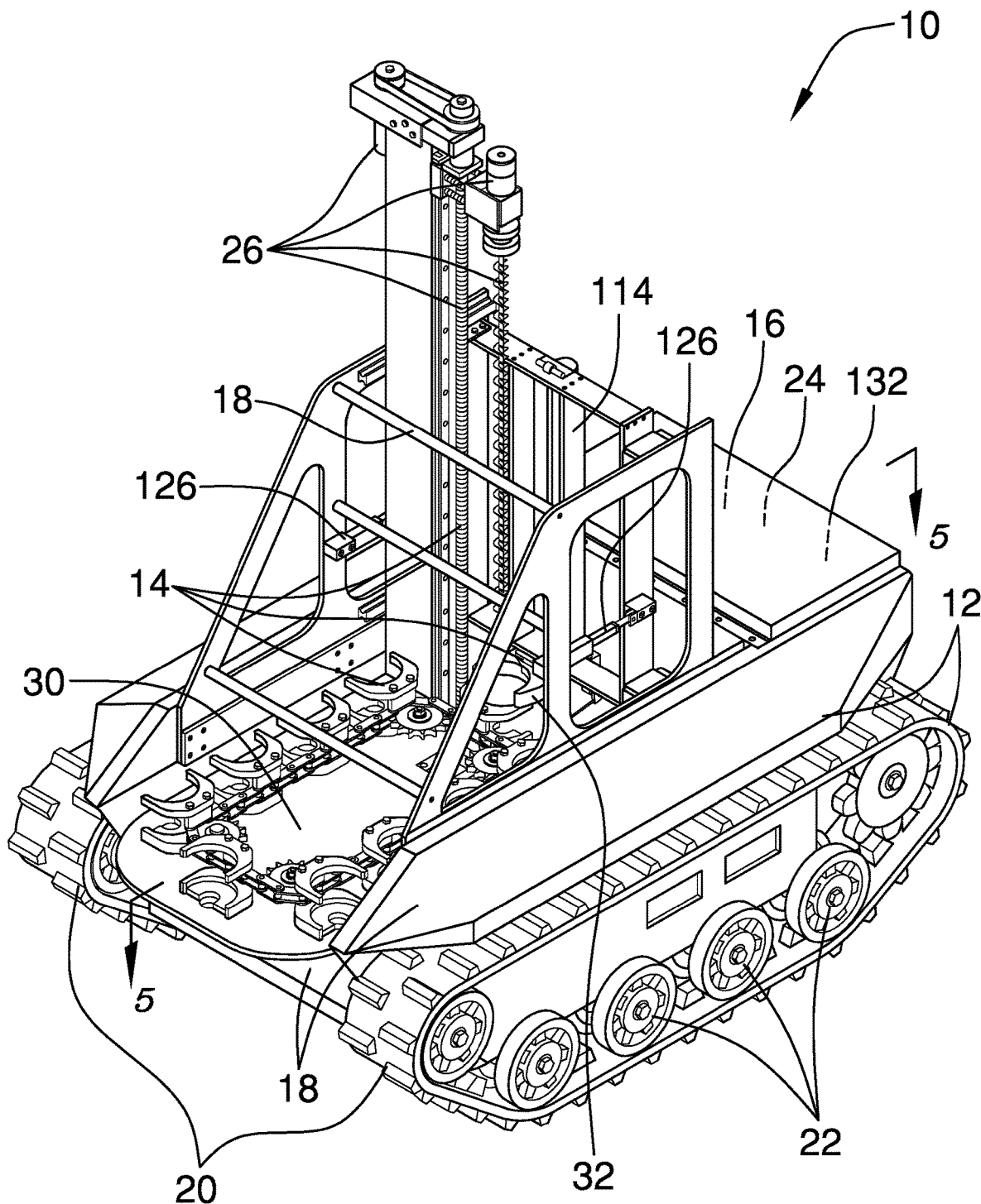
FIG. 1 is a front isometric perspective view of a robotic soil sampling assembly according to an embodiment of the disclosure.
Figure 2:
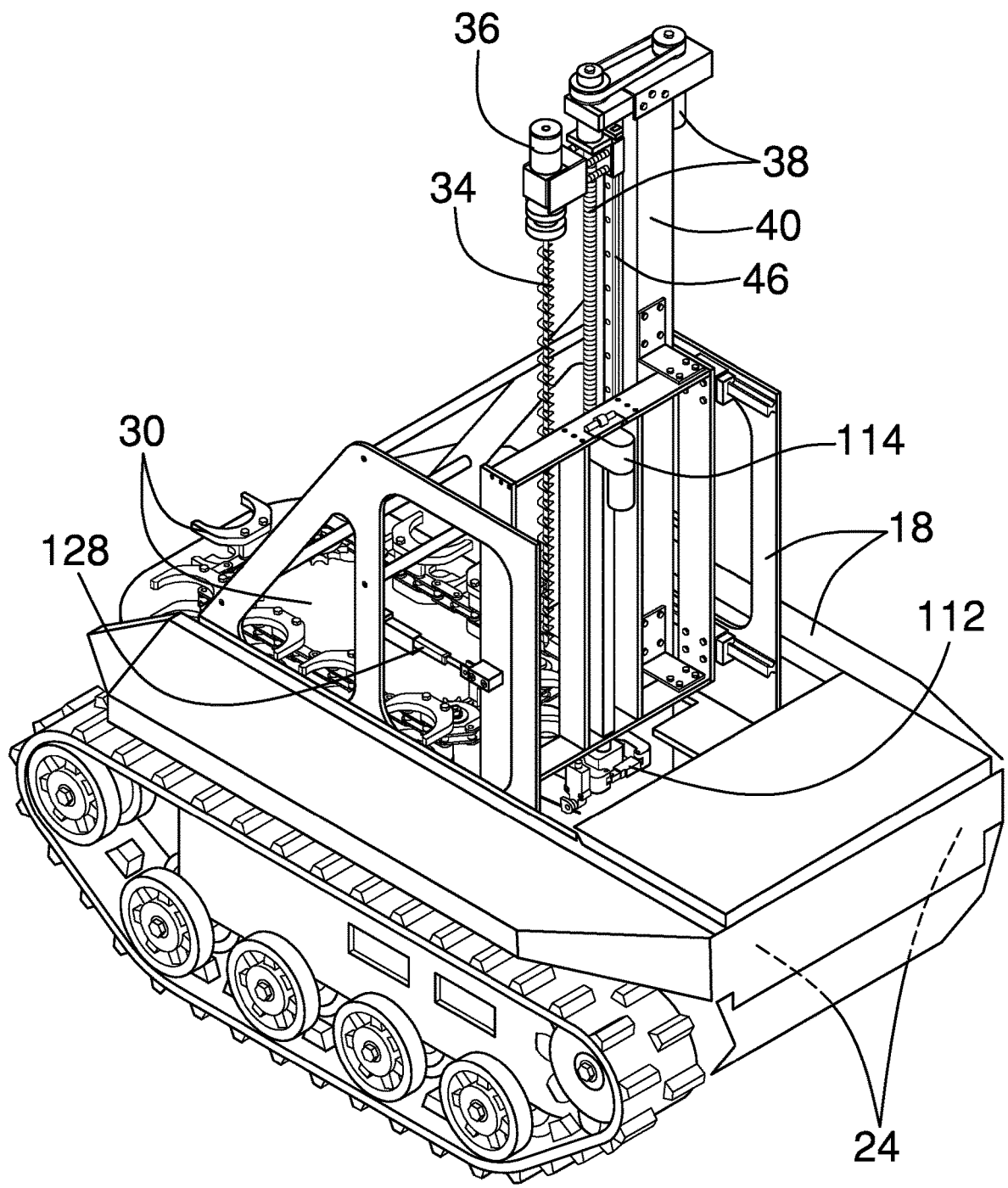
FIG. 2 is a rear isometric perspective view of an embodiment of the disclosure.

As best illustrated in FIGS. 1 through 14, the robotic soil sampling assembly 10 generally comprises a rolling chassis 12, to which a sampling apparatus 14 and a computer 16 are attached. The rolling chassis 12 may comprise a frame 18, a pair of continuous tracks 20, a plurality of wheels 22, and a pair of chassis motors 24, as is shown in FIGS. 1, 2 and 8. The present invention anticipates the continuous tracks 20 comprising rubber, silicone, metal, or the like. Other configurations of rolling chassis known in the prior art are also anticipated by the present invention, such as, but not limited to, three-wheeled rolling chassis, four wheeled rolling chassis, and the like.

The sampling apparatus 14 comprises a drill assembly 26, a plurality of containers 28, to which a robotic manager 30 is operationally engaged, and a robotic handler 32. The drill assembly 26 in turn comprises an auger 34, to which a drill motor 36 and a drill actuator 38 are operationally engaged. The drill motor 36 and a drill actuator 38 selectively rotate and drill the auger 34, respectively, into ground upon which the rolling chassis 12 is positioned. A post 40 is slidably attached to and extends from the rolling chassis 12. The drill actuator 38 may comprise a screw drive 42 and a stepper motor 44, which are attached to the post 40, or other actuating means, such as, but not limited to, hydraulic cylinders, and the like. A vertical guiderail 46, to which the auger 34 is slidably attached, is attached to and extends along the post 40. With the drill motor 36 and the stepper motor 44 actuated, the auger 34 rotates and is drilled into the ground. The auger 34 is particularly useful in obtaining soil samples 48 from hard soils.

Each container 28 comprises a tube 50 and a lid 52, with a plurality of slits 54 being positioned in the lid 52. The tube 50 has a top 56 that is open and a bottom 58 that is closed. Each extrusion 60 of a pair of extrusions 60 extends from an outer surface 62 of the tube 50 and circumferentially around the tube 50 so that the pair of extrusions 60 defines a groove 64. A pipe 66 is attached by its lower end 68 to the bottom 58 of the tube 50 and extends from a hole 70, which is axially positioned in the bottom 58 of the tube 50, toward the top 56. An upper end 72 of the pipe 66 and the top 56 of the tube 50 define a gap 74. The pipe 66 is circumferentially complementary to the auger 34 and may protrude from the bottom 58 of the tube 50, as is shown in FIG. 13. The pipe 66 protruding from the bottom 58, and being circumferentially smaller that the tube 50, forms a tighter seal with a surface of the ground and decreases a probability of soil loss from the auger 34 while sampling.

The lid 52, which comprises elastomer and thus is resiliently deformable, is selectively attachable to the tube 50 to cover the top 56. Each slit 54 extends from a center 76 of the lid 52 toward a circumference 78 of the lid 52 so that the plurality of slits 54 defines a plurality of flaps 80. As is shown in FIGS. 8-13, the auger 34 passes through the lid 52 and the pipe 66 during acquisition of a soil sample 48. As the auger 34 is drilled into the ground, soil travels up the auger 34 to the gap 74, where some of it falls off into the respective container 28. Additional soil is scraped from the auger 34 by the flaps 80 and falls into the respective container 28.

The present invention also anticipates a scraper (not shown) to provide for additional removal of soil from the auger 34 prior to subsequent sampling. The scraper could comprise, for example, another lid 52 (not shown) that is fixedly attached to the frame 18 of the rolling chassis 12 and positioned around the auger 34. The scraper also could comprise a brush (not shown), which would make contact with the auger 34 as it rotates.

The robotic manager 30 selectively positions a respective container 28 in axial alignment with the auger 34. The robotic manager 30 comprises a base plate 82 and a plurality of cogwheels 84. A void 86 extends into a first end 88 of the base plate 82. Each cogwheel 84 is rotationally and axially attached to the base plate 82 so that the cogwheels 84 are arrayed between the void 86 and a second end 90 of the base plate 82. A drive chain 92 is geardly engaged to the plurality of cogwheels 84. As is shown in FIGS. 3-6, four cogwheels 84 are attached to the base plate 82 in a rectangular configuration. The present invention also anticipates the plurality of cogwheels 84 comprising three, five, or six cogwheels 84, which could be positioned in a variety of configurations, such as, but not limited to, triangular, pentagonal, hexagonal, and the like.

A plurality of cupholders 94 is attached to the drive chain 92 so that each cupholder 94 is positioned to selectively hold a respective container 28. As is shown in FIG. 3, the plurality of cupholders 94 comprises ten cupholders 94, but other numbers of cupholders 94 are anticipated by the present invention. Each cupholder 94 may comprise an upper bracket 96 and a lower plate 98. A recess 100, which is shaped complementarily to the bottom 58 of the tube 50, is positioned in the lower plate 98. A cutout 102, which is complementary to the pipe 66, extends from the recess 100 into the lower plate 98. The respective container 28 thus is selectively insertable into the cupholder 94 to frictionally engage the respective container 28 to the cupholder 94. The present invention anticipates other cup holding means in addition to the cupholder 94, such as, but not limited to, electromagnets for use with ferromagnetic tubes, clamps, and the like.

A positioning motor 104 is attached to the base plate 82 and is operationally engaged to a respective cogwheel 84. The positioning motor 104 selectively rotates the drive chain 92 to center a respective cupholder 94 above the void 86. A positioning sensor 106, which is attached to the base plate 82 and is operationally engaged to the positioning motor 104, allows for the positioning motor 104 to be de-actuated upon centering of the respective cupholder 94 above the void 86.

With the respective container 28 centered above the void 86, the robotic handler 32 is positioned to selectively grip the respective container 28 and to selectively position the respective container 28 along an axis 108 that is defined by the auger 34. The robotic handler 32 comprises a pair of arms 110, which are mutually hingedly engaged so that the arms 110 are selectively positionable in a release configuration and a gripping configuration, as is shown in FIGS. 5 and 6, respectively. In the release configuration, the respective container 28 is insertable between and releasable from the arms 110. As is shown in FIG. 11, the groove 64 is positioned for selective insertion of the pair of arms 110. In the gripping configuration, the arms 110 grip the respective container 28 and are prevented by the extrusions 60 from sliding on the outer surface 62 of the tube 50.

The robotic handler 32 also comprises a gripping actuator 112, a gripper positioning actuator 114, and a contact sensor 116. The gripping actuator 112 is operationally engaged to the pair of arms 110 to selectively motivate the pair of arms 110 to the gripping configuration to grip the respective container 28. The gripper positioning actuator 114 is operationally engaged to the pair of arms 110 to selectively motivate the pair of arms 110 and the respective container 28 along the axis 108 that is defined by the auger 34.

The contact sensor 116 is attached to the pair of arms 110 and is operationally engaged to the gripper positioning actuator 114. The contact sensor 116 allows the gripper positioning actuator 114 to be de-actuated upon contact of the respective container 28 with the ground upon which the rolling chassis 12 is positioned. The contact sensor 116 may comprise a lever switch 118, as is shown in FIG. 12, or other contact sensing means, such as, but not limited to, proximity sensors, photodetectors, and the like.

The gripping actuator 112 may comprise a horizontally mounted linear actuator 120, as is shown in FIG. 4, while the gripper positioning actuator 114 may comprise a vertically mounted linear actuator 122, as is shown in FIG. 10, although the present invention also anticipates other actuating means for fulfilling these purposes, as are known to those skilled in the art of robotic actuators.

The drill assembly 26 and the robotic handler 32 are slidably attached to a pair of horizontal guiderails 124, which are attached to the frame 18. An apparatus positioning actuator 126, which is operationally engaged to the drill assembly 26 and the robotic handler 32, allows for selective separation of the drill assembly 26 and the robotic handler 32 from the robotic manager 30, as can be seen when comparing the position of the drill assembly 26 and the robotic handler 32 in FIG. 8 relative to that in FIG. 10. The apparatus positioning actuator 126 may comprise a horizontal linear actuator 128, or other actuating means known to those skilled in the art of robotic actuators.

The computer 16, to which a location transceiver 130 is operationally engaged, is operationally engaged to the rolling chassis 12 and to the sampling apparatus 14. The location transceiver 130 is Global Positioning System enabled so that the computer 16 can send and receive positional coordinates via the location transceiver 130. The computer 16 is programmable to selectively actuate the pair of chassis motors 24 to sequentially position the rolling chassis 12 at sampling sites. Providing more power to one chassis motor 132 relative to the other chassis motor 132 effective turns the rolling chassis 12. The computer 16 is programmable to selectively actuate the sampling apparatus 14 to obtain a soil sample 48 at each sampling site and to deposit the soil sample 48 in an associated container 28. The present invention also anticipates a communications transceiver (not shown) being operationally engaged to the computer 16. The communications transceiver would allow for wireless communication between an operator and the computer 16.

The present invention anticipates the robotic soil sampling assembly 10 being powered by a battery 132, although other power sources, such as, but not limited to, gas fired engines, diesel fired engines, or the like, are also anticipated.

The present invention anticipates a method of obtaining soil samples 48 using a robotic soil sampling assembly 10. The method comprises a first step of attaching a plurality of containers 28 to a robotic manager 30 of the robotic soil sampling assembly. A second step of the method is entering a plurality of positional coordinates into a computer 16 of the robotic soil sampling assembly. Each pair of positional coordinates corresponds to a respective sample site of a plurality of sample sites. A third step of the method is programming the computer 16 to follow a course from a starting point through each of the plurality of sample sites and back to the starting point, or to an alternate point.

At each sampling site, a respective container 28 is positioned in the void 86 by the robotic manager 30 and is engaged by the robotic handler 32. The auger 34 then is drilled through the lid 52 and the pipe 66 to the bottom 58 of the container 28. The apparatus positioning actuator 126 then moves the drill assembly 26 and the robotic handler 32 away from the robotic manager 30 to allow for free movement. The auger 34 and the respective container 28 are lowered into contact with the ground, at which point rotation of the auger 34 and downward pressure from the drill actuator 38 cause the auger 34 to penetrate the ground and to lift a soil sample 48 up through the pipe 66 and into the container 28. After the soil sample 48 is obtained, the auger 34 and the respective container 28 are raised and the robotic handler 32 returns the respective container 28 to the robotic manager 30 to start the process anew.

A fourth step of the method is removing the plurality of containers 28 from the robotic manager 30. The soil samples 48 from the containers 28 then can subjected to analysis or sent to a soils lab for analysis.

The present invention also anticipates the method comprising an additional step of programming the computer 16 to selectively actuate a drill actuator 38 of the robotic soil sampling assembly to obtain the soil samples 48 at a specified depth, such as, but not limited to, from approximately 0.0 to 15.3 cm, from approximately 15.3 to 61.0 cm, or the like. Furthermore, the present invention also anticipates the course from the starting point through each of the plurality of sample sites and back to the starting point being calculated by the computer 16.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A robotic soil sampling assembly comprising:
   a rolling chassis;
   a sampling apparatus attached to the rolling chassis, the sampling apparatus comprising:
   a drill assembly comprising:
      an auger,
      a drill motor operationally engaged to the auger for selectively rotating the auger, and
      a drill actuator operationally engaged to the auger for selectively drilling the auger into ground upon which the rolling chassis is positioned,
   a plurality of containers,
   a robotic manager operationally engaged to the plurality of containers, such that a respective container is selectively positionable in axial alignment with the auger, and a robotic handler positioned for selectively gripping the respective container and for selectively positioning the respective container along an axis defined by the auger; and a computer attached to the rolling chassis, the computer being operationally engaged to the rolling chassis and the sampling apparatus, the computer being programmable for selectively actuating a pair of chassis motors for sequentially positioning the rolling chassis at sampling sites and for selectively actuating the sampling apparatus for obtaining a soil sample at each sampling site and for depositing the soil sample in an associated container.

2. The robotic soil sampling assembly of claim 1, wherein the rolling chassis comprises a frame, a pair of continuous tracks, a plurality of wheels, and a pair of chassis motors.

3. The robotic soil sampling assembly of claim 1, further including:
a post slidably attached to and extending from the rolling chassis;
the drill actuator comprising a screw drive and a stepper motor attached to the post; and
a vertical guiderail attached to and extending along the post, the auger being slidably attached to the vertical guiderail.

4. The robotic soil sampling assembly of claim 1, wherein each container comprises:
a tube having a top and a bottom, the top being open, the bottom being closed;
a hole axially positioned in the bottom of the tube;
a pipe having a lower end attached to the bottom of the tube and extending from the hole toward the top, defining a gap between an upper end of the pipe and the top of the tube, the pipe being circumferentially complementary to the auger;
a lid selectively attachable to the tube for covering the top, the lid comprising elastomer, such that the lid is resiliently deformable; and
a plurality of slits positioned in the lid, each slit extending from a center of the lid toward a circumference of the lid, such that the plurality of slits defines a plurality of flaps.

5. The robotic soil sampling assembly of claim 4, wherein the robotic manager comprises:
a base plate;
a void extending into a first end of the base plate;
a plurality of cogwheels, each cogwheel being rotationally and axially attached to the base plate, such that the cogwheels are arrayed between the void and a second end of the base plate;
a drive chain gearedly engaged to the plurality of cogwheels;
a plurality of cupholders attached to the drive chain, such that each cupholder is positioned for selectively holding a respective container; and
a positioning motor attached to the base plate and operationally engaged to a respective cogwheel, such that the positioning motor is positioned for selectively rotating the drive chain for centering a respective cupholder above the void.

6. The robotic soil sampling assembly of claim 5, further including a positioning sensor attached to the base plate and operationally engaged to the positioning motor, such that the positioning motor is de-actuated upon centering of the respective cupholder above the void.

7. The robotic soil sampling assembly of claim 5, wherein the pipe protrudes from the bottom of the tube; and each cupholder comprises:
an upper bracket,
a lower plate,
a recess positioned in the lower plate and shaped complementarily to the bottom of the tube, and
a cutout extending from the recess into the lower plate, the cutout being complementary to the pipe, such that the respective container is selectively insertable into the cupholder for frictionally engaging the respective container to the cupholder.

8. The robotic soil sampling assembly of claim 4, wherein the robotic handler comprises:
a pair of arms, the arms being mutually hingedly engaged, such that the arms are selectively positionable in a release configuration, wherein the respective container is insertable between and releasable from the arms, and a gripping configuration, wherein the arms grip the respective container;
a gripping actuator operationally engaged to the pair of arms for selectively motivating the pair of arms to the gripping configuration for gripping the respective container;
a gripper positioning actuator operationally engaged to the pair of arms for selectively motivating the pair of arms and the respective container along the axis defined by the auger; and
a contact sensor attached to the pair of arms and operationally engaged to the gripper positioning actuator, such that the gripper positioning actuator is deactuated upon contact of the respective container with the ground upon which the rolling chassis is positioned.

9. The robotic soil sampling assembly of claim 8, wherein:
the gripping actuator comprising a horizontally mounted linear actuator; and
the gripper positioning actuator comprising a vertically mounted linear actuator.

10. The robotic soil sampling assembly of claim 8, further including a pair of extrusions, each extrusion extending from an outer surface of the tube and circumferentially around the tube, such that the pair of extrusions defines a groove positioned for selective insertion of the pair of arms.

11. The robotic soil sampling assembly of claim 1, further including an apparatus positioning actuator operationally engaged to the drill assembly and the robotic handler for separating the drill assembly and the robotic handler from the robotic manager.

12. The robotic soil sampling assembly of claim 11, further including:
the apparatus positioning actuator comprising a horizontal linear actuator; and
a pair of horizontal guide rails attached to a frame of the rolling chassis, the drill assembly and the robotic handler being slidably attached to the pair of horizontal guiderails.

13. The robotic soil sampling assembly of claim 1, further including a location transceiver operationally engaged to the computer, the location transceiver being Global Positioning System enabled, such that the computer is enabled for sending and receiving positional coordinates via the location transceiver.

14. A method of obtaining soil samples using a robotic soil sampling assembly, the method comprising the steps of:
attaching a plurality of containers to a robotic manager of the robotic soil sampling assembly;
entering a plurality of positional coordinates into a computer of the robotic soil sampling assembly, wherein each pair of positional coordinates corresponds to a respective sample site of a plurality of sample sites;

programming the computer for selectively actuating a drill actuator of the robotic soil sampling assembly for obtaining the soil samples at a specified depth;

programming the computer to follow a course from a starting point through each of the plurality of sample sites and back to the starting point or to an alternate point; and removing the plurality of containers from the robotic manager.

15. The method of obtaining soil samples of claim 14, wherein the course from the starting point through each of the plurality of sample sites and back to the starting point is calculated by the computer.

* * * * *